United States Patent [19]

Driller et al.

[11] Patent Number: 4,484,569

[45] Date of Patent: Nov. 27, 1984

[54] ULTRASONIC DIAGNOSTIC AND THERAPEUTIC TRANSDUCER ASSEMBLY AND METHOD FOR USING

[75] Inventors: Jack Driller, Ridgewood, N.J.; William G. Henriksen, Hauppauge, N.Y.; D. Jackson Coleman, Haworth; Frederic L. Lizzi, Tenafly, both of N.J.

[73] Assignee: Riverside Research Institute, New York; Cornell Research Foundation, Inc., Ithaca, both of N.Y.

[21] Appl. No.: 353,506

[22] Filed: Mar. 1, 1982

[30] Foreign Application Priority Data

Mar. 13, 1981 [CS] Czechoslovakia .................... 1836-81

[51] Int. Cl.$^3$ ............................................. A61B 10/00
[52] U.S. Cl. .................................. 128/660; 128/24 A
[58] Field of Search ................ 128/660, 745, 661, 663

[56] References Cited

U.S. PATENT DOCUMENTS

| | | | |
|---|---|---|---|
| 3,237,623 | 3/1960 | Gordon | 128/24 |
| 3,735,755 | 5/1973 | Eggleton et al. | 128/24 A |
| 4,237,901 | 12/1980 | Toenzer | 128/660 |
| 4,316,271 | 2/1982 | Evert | 128/660 X |

OTHER PUBLICATIONS

"Effects of Prenatal Exposure to Ultrasound", by Sikov et al., *Advances in the Study of Birth Defects*, vol. 2, *Teratological Testing*, Ed. by T.V.N. Persaud, M.T.P. Press Ltd., Lancaster, England, 1979, pp. 267–273.

"Applications of Therapeutic Ultrasound in Ophthalmology", by Coleman, et al., *Progress in Medical Ultrasound*, vol. 2/1981, Ed. by A. Kurjak, Excerpta Medica, Amsterdam-Oxford-Princeton, published Mar. 1981.

"Experimental Cataract Production by High Frequency Ultrasound", by Lizzi et al., *Annals of Ophthalmology*, vol. 10, #7, Jul. 1978.

"Ultrasonically Accelerated Resorption of Vitreous Membranes", by Coleman et al., *American Journal of Ophthalmology*, vol. 89, No. 4, Apr. 1980.

"Effects of Pulsed Ultrasound on Ocular Tissue", by Lizzi et al., *Ultrasound in Med. & Biol.*, vol. 7, pp. 245–252, 1981.

"Experimental, Ultrasonically Induced Lesions in the Retina, Choroid, and Sclera", by Lizzi et al., *Investigative Ophthalmology & Visual Science*, St. Louis, vol. 17, No. 4, pp. 350–360, Apr. 1978.

"Therapeutic Ultrasound in the Production of Ocular Lesions", by Coleman et al., *American Journal of Ophthalmology*, vol. 86, No. 2, Aug. 1978, pp. 185–192.

"Potential Therapeutic Applications of Ultrasound in Ophthamology", by Lizzi et al., *XII International Conference on Med. & Biol. Engineering*, Jerusalem, Israel, Aug. 1979.

"Vitreous Liquefaction by Ultrasound", by Coleman et al., Chap. 43, *Ophthalmic Ultrasound*, C. V. Morby Co., 1969, pp. 337–342.

"Production of Alternate Filtration Paths for Treatment of Glaucoma with High-Intensity Focused Ultrasound", Paper #1303, by Coleman et al., AIUM 1981, p. 116.

"Experimental Treatment of Intra-Ocular Carcinoma with High-Intensity Focused Ultrasound", by F. L. Lizzi et al., Paper #1305, AIUM 1980, p. 46.

"Experimental Investigation Into Glaucoma Treatment Using High-Intensity Focused Ultrasound", Paper #1301, by D. J. Coleman et al., AIUM 1979, p. 47.

(List continued on next page.)

*Primary Examiner*—Kyle L. Howell
*Assistant Examiner*—Francis J. Jaworski
*Attorney, Agent, or Firm*—Brumbaugh, Graves, Donohue & Raymond

[57] ABSTRACT

An ultrasonic transducer assembly is provided with transducers for both therapeutic and diagnostic ultrasonic radiation. A moveable seal permits adjustment and alignment of the two transducer units in a fluid medium. In addition, there is provided a light beam directed along the axis of the ultrasonic radiation. The transducer assembly is particularly useful for ophthalmic therapy.

20 Claims, 5 Drawing Figures

OTHER PUBLICATIONS

"Ultrasonically Facilitated Resorption of Vitreous Membranes", by F. L. Lizzi et al., AIUM 1978, p. 74.

"Effect of Focused Ultrasound on Thin Membranes Within the Eye", by F. L. Lizzi et al., 1979, vol. 65, Suppl. #1, p. S5.

"Experimental Production of Chorioretinal Lesions", by F. L. Lizzi et al., AIUM 1977-#1109, pp. 579-581.

"Experimental Production of Chorioretinal Lesions", by D. J. Coleman et al., AIUM 1977-#1111, pp. 575-578.

"Animal Studies of Cataracts Produced by High-Intensity Ultrasonic Energy", by F. L. Lizzi et al., AIUM 75, pp. 525-526.

"Privileged Communication", by F. L. Lizzi, #087-3-4-2819, pp. 50-54.

ULTRASONIC DIAGNOSTIC AND THERAPEUTIC TRANSDUCER ASSEMBLY AND METHOD FOR USING

The invention described herein was made in the course of work under a grant or award from the Department of Health, Education and Welfare.

BACKGROUND OF THE INVENTION

This invention relates to the application of ultrasonic waves for diagnostic and therapeutic purposes. The invention particularly relates to the application of ultrasonic waves for purposes of diagnosing disorders of the eye and treating such disorders by non-invasive ultrasonic treatment. In particular this application relates to transducers for performing such diagnosis and treatment.

It is an object of the present invention to provide a new and improved transducer assembly which provides for application of both therapeutic and diagnostic ultrasonic waves to a human or animal body.

It is a further object of the invention to provide such a transducer assembly wherein the therapeutic and diagnostic waves are directed substantially along a single axis.

It is a further object of the invention to provide such a transducer assembly which includes a source of a light beam directed along the axis with the therapeutic and diagnostic ultrasonic beams.

SUMMARY OF THE INVENTION

In accordance with the invention there is provided an ultrasonic transducer assembly, useful for non-invasive applications, comprising a housing and a transducer means mounted within the housing for radiating a converging beam of acoustic energy in response to supplied electrical signals. The beam of acoustic energy converges to a focal point. The transducer has a central bore and there is provided a light source mounted within the housing and through the central bore of the transducer for emitting the light beam toward the focal point.

In one embodiment the transducer comprises a spherical shell portion having an inner radius originating at the focal point. The housing includes means for maintaining fluid in contact with the transducer thereby to conduct the beam of acoustic energy from the transducer into a body.

In a particularly advantageous embodiment, the transducer assembly includes first and second housing portions, and first and second transducers coaxially mounted to the respective housing portions. The light source can be mounted through a central aperture in the inner one of the two transducers. The first and second housing portions can be pivotably mounted to each other thereby to adjust the direction of the beams from the first and second acoustic transducers to be along the same axis as the light beam.

For a better understanding of the present invention, together with other and further objects, reference is made to the following description, taken in conjunction with the accompanying drawings, and its scope will be pointed out in the appended claims.

DESCRIPTION OF THE INVENTION

Figure 1:
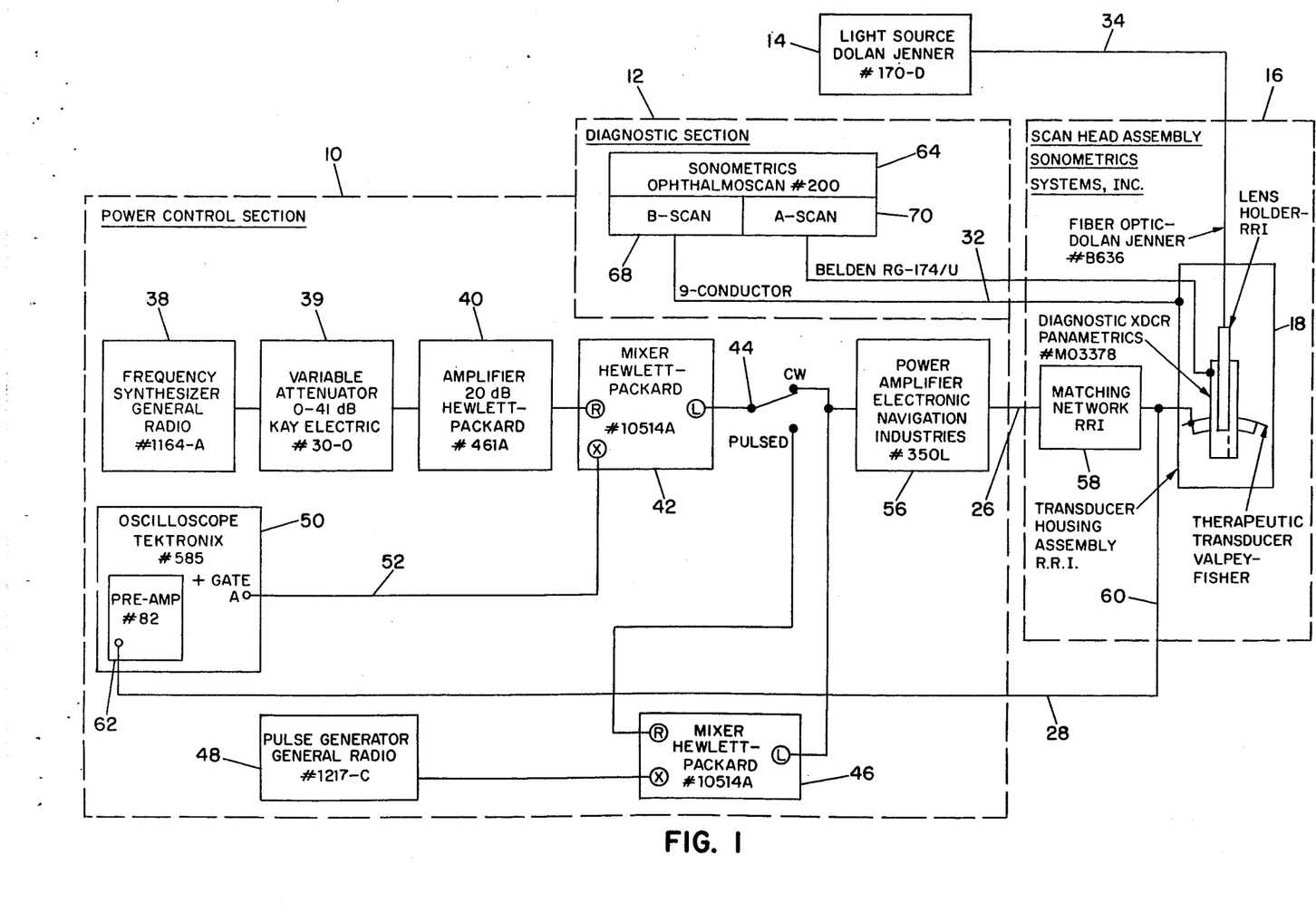
FIG. 1 is a block diagram of a system for the application of therapeutic and diagnostic ultrasound to a human or animal eye.

The block diagram of FIG. 1 illustrates a system for applying diagnostic and therapeutic ultrasound to the eye of a human or an animal patient. The system of FIG. 1 includes a power control section 10, a diagnostic section 12, a scan head assembly 16 and a light source 14. The power control section 10 functions to provide controlled, relatively high power, bursts of ultrasonic energy to the therapeutic transducer 28 which is included in the transducer assembly 18 of the scan head assembly 16. The diagnostic section 12 operates in conjunction with the diagnostic transducer unit 22 of the transducer assembly 18. The light source 14 provides a light beam through a fiber optic conduit 34 to a central light tube and lens holder 24 in the transducer assembly 18.

The system of FIG. 1 functions to provide both diagnostic probing of an eye or other organ, visual indication by a light beam of the probe orientation, and a therapeutic ultrasonic radiation for performing noninvasive surgery, for example, in treating diseases of the human eye or an animal eye.

The power control section 10 includes a frequency synthesizer 38 for generating a high frequency ultrasonic signal, for example, approximately 4 to 10 Mhz. Illustrated in FIG. 1 is a General Radio Model 1164-A frequency synthesizer. The output from frequency synthesizer 38 is provided to variable attenuator 39, for example, Kay Electric Model 30-0. Following variable attenuator 39 there is provided an amplifier 40 which is a Hewlett Packard Model 461 A. By use of the frequency synthesizer 38, variable attenuator 39 and amplifier 40 it is possible to provide a controlled amplitude signal at a selected ultrasonic frequency. The output signal of amplifier 40 is provided to a gate or mixer 42, which is a Hewlett Packard Model 10514 A. Also provided to mixer 42 over lead 52 is a gating signal from a Tektronix oscilloscope Model 585. The gating signal is used to provide a controlled duration for the signal at the output of amplifier 40. Typically the controlled pulse would have a duration of 5 seconds. A switch 44 is provided to alternately operate the power control section 10 as either a CW or pulsed power supply. When switch 44 is in the CW position the output of mixer 42 is provided directly to power amplifier 56 which is an Electronic Navigation Industries Model 350 L. When pulsed power is desired, switch 44 is placed in the lower position so that the output of mixer 42 is provided to gate or mixer 46, which is also provided with pulse signals from a pulse generator 48, which is a General Radio Model 1217-C. The output from mixer 46 is a pulse modulated signal having a fundamental ultrasonic frequency determined by frequency synthesizer 38.

Power amplifier 56 is provided to increase the power of the CW or pulsed signal provided thereto, and provide a high power signal over coaxial cable 26, which is RG 58/U cable, to the transducer assembly 18 through a matching network 58. The RF power provided to a matching network 58 can be in the order of 20 watts and can achieve an acoustic power output from the transducer assembly 18 in the order of 5 to 10 watts. Matching network 58 includes a lead 60, also RG 58/U cable to provide a portion of the RF signal to preamplifier 62 on oscilloscope 50 so that the power supplied to the transducer by the matching network can be monitored on the oscilloscope display.

Figure 2:
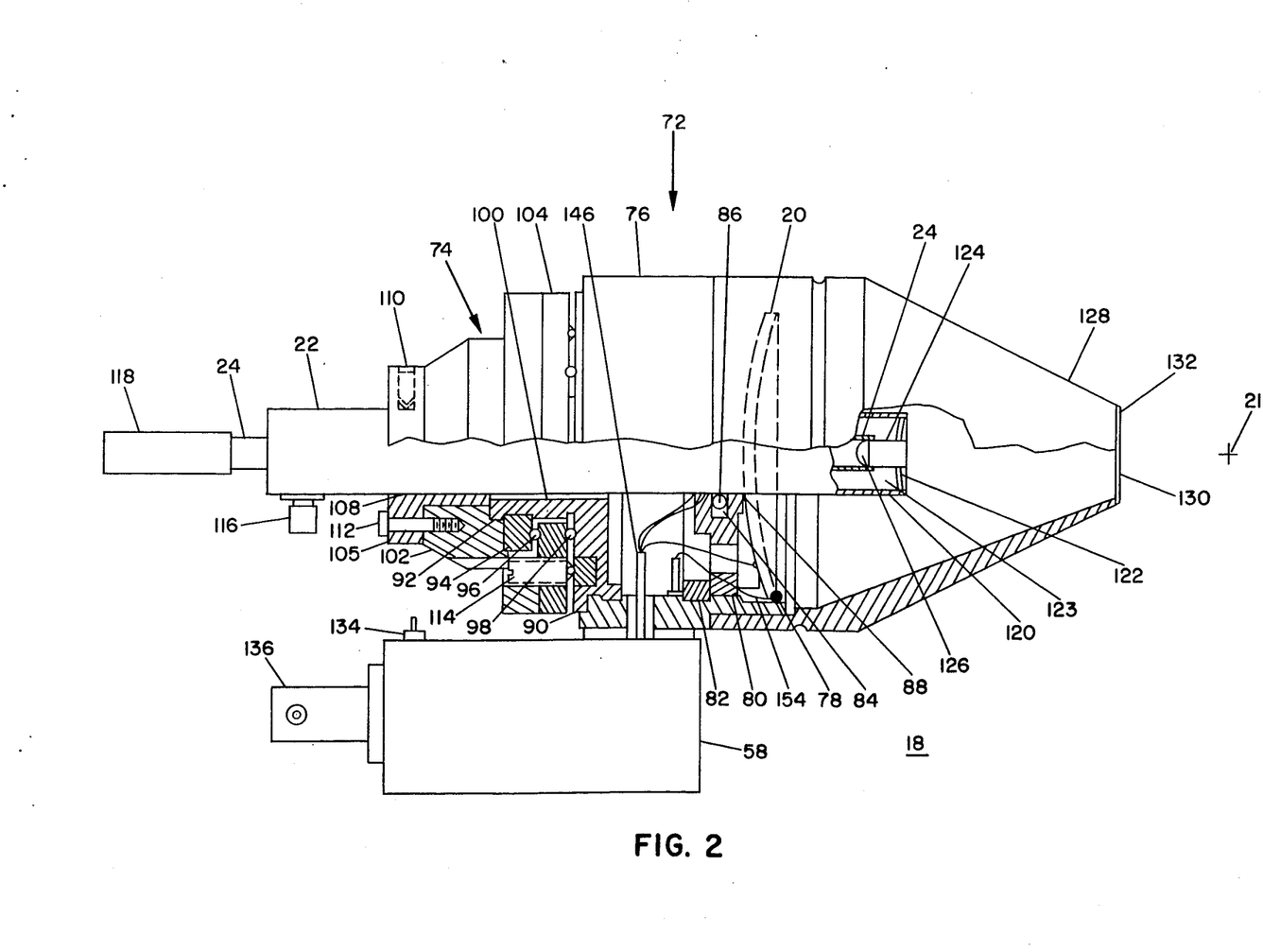
FIG. 2 is a side, partial cross section view of the transducer assembly used in the system of FIG. 1.

The output of matching network 58 is coupled to the therapeutic transducer 20 in transducer assembly 18 which will be further described with respect to FIG. 2.

The diagnostic section 12 of the system of FIG. 1 primarily consists of a Sonometrics Ophthalmoscan Model 200 unit. This unit 64 includes an A scan display 70 and a B scan display 68 which are coupled to position encoding units mounted on a scan head assembly by a 9 conductor wire 32 for providing angular positioning information relating to the orientation of diagnostic transducer unit 22. The Ophthalmoscan unit 64 is also connected to diagnostic transducer unit 22 by cable 30 which is a Belden type RG 174/U coaxial cable.

Transducer assembly 18 also includes a lens holder 24 which is connected to a light source 14 by a fiber optic cable 34. As is familiar to those in the art, the scan head assembly 16 includes position sensors which provide the signal over the 9 conductor wire to the Ophthalmoscan unit 64. A scan head assembly which includes the position sensors is made by Sonometric Systems.

FIG. 2 is a side and partial cross section view of the transducer assembly 18 of the system of FIG. 1. The assembly 18 of FIG. 2 includes three active components, which are the therapeutic transducer 20, the diagnostic transducer 22 and the light beam assembly and lens holder 24. Also illustrated in FIG. 2, attached to transducer assembly 18 is the matching network 58 which serves to provide an impedance match of the transducer 20 to the impedance existing at the cable 26 through which signals are supplied from power amplifier 56. Those skilled in the art will recognize that the matching network 58 will have inductive and/or capacitive components for the purposes of impedance matching the transducer according to the frequency of operation. In one embodiment, the matching network 58 includes a series inductor and a shunt capacitor. Therapeutic transducer 20 comprises a spherical shell section having an inner radius which originates at a focal point 21. The inner and outer radial surfaces of transducer 20 are metal clad, and the transducer itself is made of piezoelectric material, typically a ceramic such as lead zirconate titanate. In one embodiment the thickness of the transducer is chosen to be resonant at 1.4 Mhz. The transducer may be operated at an odd harmonic, for example, the third or seventh harmonic, to provide a therapeutic ultrasonic signal at a frequency of 4.2 Mhz. for the third harmonic or 9.8 Mhz for the seventh harmonic.

The transducer 20 is mounted within a first housing portion 72 of the transducer assembly. The first housing portion 72 includes a housing member 76 of generally cylindrical configuration. Housing member 76 engages transducer 20 at one cylindrical end and is sealed to the transducer by a bead of silicon rubber 78, which provides for physical attachment of the transducer as well.

Figure 3:
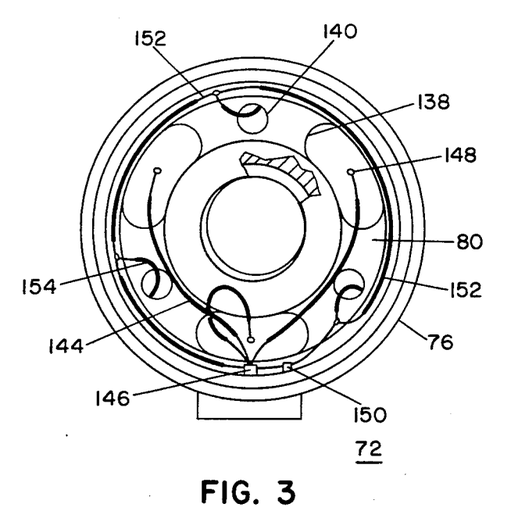
FIG. 3 is a rear view of a portion of the transducer shown in FIG. 2.
Figure 4:
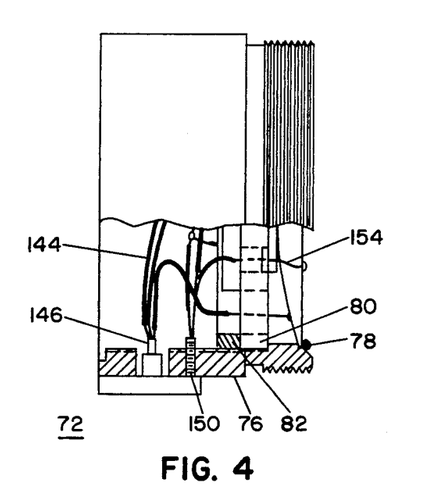
FIG. 4 is a side, partial cross section view of the section shown in FIG. 3.

Transducer 20 has a central bore through which diagnostic transducer unit 22 passes. Transducer 20 is mounted around the central bore by a similar bead 88 of silicon rubber cement to a support member 80. Support member 80 is retained within housing member 76 by a cylindrical retaining ring 82 which is threaded into internal threads in housing member 76, as may be more easily seen in the view of the housing portion 72 shown in FIGS. 3 and 4.

Transducer 20 has its radially outer conductive surface connected to inner conductor terminal 146 which leads to matching network 58. This connection is made by lead wires 144 which are conductively attached to the surface at points 148.

The radially inner, and radiating surface of transducer 20 is connected to the outer conductor terminal 150 leading to matching network 58. This connection is made by lead wires 154, which are connected to a ring bus 152 leading to terminal 150. The wires 154 and 144 pass through apertures 138 and 140 in support member 80. The wires 154 which lead to the radially inner, and radiating surface of transducer 20 also pass through recesses 78 formed in housing member 76. This connection is more easily seen in the cross sectional view of FIG. 2, which is taken through one of these recesses.

Support member 80 is provided with a central bore, which is aligned with the central bore of transducer 20 and sealed thereto by the bead of silicon rubber 88. Diagnostic transducer unit 22 is cylindrical in shape and passes through the central bore in support member 80 and in transducer 20. Diagnostic transducer 22 can project outwardly from therapeutic transducer 20 into a cavity formed by conical shell 128, which is provided to retain fluid, such as water, in the vicinity of transducers 20 and 22, in order to provide a medium for effective radiation of ultrasound from the transducers. Since conical member 128 and the cavity formed thereby is to be filled with fluid the front opening 130 is covered by a membrane 132, preferably of thin rubber, and the rear portion is sealed by the beads 78 and 88 on transducer 20. To provide sealing where transducer 22 passes through support member 80 there is provided a radially extending groove 84 in support member 80 within which there is provided an O-ring 86 engaging transducer 22. Groove 84 is made substantially deeper than necessary to accomodate O-ring 86, and is filled with a viscous fluid, such as petroleum jelly, to allow for movement of O-ring 86 radially within groove 84. This provides a relatively moveable seal between transducer 22 and support member 80. This moveable seal is required because of the adjustable nature of the transducer orientation, as will be further described. Conical shell 128 is sealed to housing member 76 by a tightly fitting thread at the junction between these two parts.

At the end of housing portion 72 opposite conical shell 128 there is provided a mounting member 90 for connecting the first housing portion 72 to the second housing portion 74. Mounting member 90 may be made of aluminum or similar material, and includes an axially extending cylindrical section 92 which extends within housing portion 74. Mounted on cylindrical section 92 is a retaining ring 94. This retainer ring also loads the O-rings 96 and 98 under compression to permit pivotal adjustment of transducer 20 about transducer 122. The loading of said O-rings between 100, 104 and 94 adds to the sensitivity of pivotal adjustment, and keeps the pivot adjusting screws under tension maintaining any adjustment that is made. Flange 104 is fixedly connected, for example, by screws to housing member 102 of housing portion 74. Also provided on housing portion 74 is a retaining sleeve 105 which has a central cylindrical bore 108 which is closely fitted around transducer unit 22 and secured thereto by means of one or more set screws 110. Sleeve 105 is mounted to housing member 102 by screws 112. As illustrated in FIG. 2, transducer unit 22 extends from mounting sleeve 105 through a central bore 100 in mounting member 90 and thence through mounting member 80 and transducer 20 to project into the cavity which is fluid filled and enclosed by conical shell 128. Transducer 122 in unit 22 is held stationary in place. Pivotal adjustment is made to align the therapeutic transducer to transducer 122. Transducer unit 22 is axially adjustable to position the focal point of the radiating transducer 122 to have an axial location which corresponds to the location of focal point 21 of transducer 20. By reason of the pivotal connection between housing member 72 and housing member 74, there may be provided a pivoting adjustment between housing members and therefore between the axis of radiation from transducer 20 and transducer 122. This adjustment is effected by the use of set screws 114 threaded into flange 104. Typically three such set screws may be arranged at 90° intervals around flange 104. As illustrated mounting member 90 also includes hardened steel pads adjacent set screws 114 for preventing distortion of the mounting member by the action of the set screws.

Transducer unit 22 includes a radiating transducer 122 which consists of a spherical shell portion of piezoelectric material having inner and outer radial surfaces coated with conductive material and connected to the inner and outer conductors of the diagnostic signal input connector 116. The transducer 122 may alternatively comprise a flat disk, possibly with an acoustically focusing lens. The diagnostic transducer is within a metallic tube 120 within which there may be provided an ultrasonic dampening material 123 to provide for broadband operation of the transducer. Typically, the transducer operates at a nominal frequency of 7.5 Mhz. to accommodate the Sonometrics Ophthalmoscan unit, which has a broadband of operation by reason of relatively short pulses of about 0.25 microseconds. The transducer 22 has a central bore including a stepped portion which receives the lens mounting metallic tube 24 and a front portion 124 which allows light to pass through the diagnostic transducer 122. Tube 24 includes at its forwrd end adjacent to the radiating portion of transducer 122 a lens 126 which is designed to focus light, provided through optical coupling member 118 from a fiber optic light path 34 connected thereto, into a light beam which passes in a fluid medium in the direction of the radiated ultrasonic beam from diagnostic transducer unit 22. As illustrated in FIG. 2 there is provided a connector 116 for connecting the diagnostic transducer to the Ophthalmoscan unit 64. There is also provided a connector 136 on matching network 58 for connecting the power amplifier 56 to the matching network and therapeutic transducer. Also provided is a connector 134 for sampling the power provided by the matching network to the therapeutic transducer and providing that sample over lead 60 to oscilloscope 50.

As becomes evident from the foregoing description the transducer assembly 18 includes apparatus for providing three radiations, the therapeutic ultrasonic beam from transducer 20, the diagnostic ultrasonic beam from transducer unit 22 and a light beam provided through lens 126 which is supplied over the fiber optic conduit 34. Ideally all of these radiations are along the same axis, which is the axis of the transducer assembly 18, in particular, the circular and conical parts thereof.

Prior to use of the transducer assembly 18, the two housing portions 72 and 74 are adjusted so that the beams from transducers 20 and 22 will be along a common axis. In particular, using a conventional beam detecting system, the direction of radiation from each of the transducers is measured and set screws 114 are adjusted so that the beams have a common axis. This adjustment causes the pivoting of housing portions 72 and 74 with respect to each other at the junction between the housing portions which is bridged by O-rings 96 and 98. Housing member 72 has an enlarged central bore 100 at the rear mounting member 90 and has a special adjustable sealing member formed by O-ring 86 and toroidal groove 84 to permit the pivoting of transducer unit 22 within housing member 72.

An additional adjustment may be performed to provide for a common focal point of therapeutic transducer 20 and diagnostic transducer unit 22. In particular, the axial location of diagnostic transducer unit 22 can be adjusted by loosening set screws 110 and axially sliding transducer unit 22 to a position such that it has a common focal point with therapeutic transducer 20, for example, focal point 21.

Following adjustment of the axial positions and orientations of the housing members to achieve coincidence of the radiated beams on a common focal point and along a common axis, the assembly may be prepared for use by placing a membrane 132 over the opening 130 at the end of conical shell 128 after the cavity formed within shell 128 is appropriately filled with fluid to efficiently conduct ultrasonic radiation from transducers 20 and 22.

When used in connection with eye treatment, the patient is prepared by adhesively attaching a drape having a central aperture to the skin around the eye to be examined and treated. The drape is filled with a fluid and the transducer assembly, in particular, end 130 is placed within the fluid so that there is a continuous fluid path through the fluid filled cavity formed by conical shell 128, through the fluid within the drape, and into the patient's eye. When the transducer assembly is so arranged, and the transducer assembly is mounted on a conventional scanning apparatus, it becomes possible for the practitioner to adjust the position and orientation of the transducer for purposes of generating A scan and B scan images on the Ophthalmoscan unit 64 thereby to explore the tissue structure of the eye of the patient being treated. Once the tissue structure has been so explored and images displayed to the practitioner, it may be desirable to use ultrasonic beams to perform noninvasive treatment for the eye.

The transducer assembly 18 shown in FIG. 2 is particularly useful by reason of the fact that the therapeutic transducer 20 radiates a converging beam of acoustical energy which has a high energy density only in the vicinity of the focal point 21 of the beam. Accordingly, the transducer radiation from transducer 20 will pass with relatively low radiation power density through the fluid within shell 128, the fluid within the drape, and portions of tissue between focal point 21 and opening 130. Energy will be highly concentrated only at the focal point 21, and can develop at that point a localized heating or other physical effect, to provide tissue modification at the focal point and thereby provide noninvasive ultrasonic treatment to portions of the eye or other organ to which the radiation is applied. During the radiation of a therapeutic ultrasonic beam, the transducer assembly 18 is held stationary and oriented toward the point at which tissue modification is to be made. The power control section 10 shown in FIG. 1 provides a controlled, for example 5 second, burst of high energy acoustic radiation which provides the therapeutic effect. The A scan display on the Ophthalmoscan unit can be used by the physician for purposes of locating focal point 21 precisely at the tissue to be treated by the therapeutic radiation beam.

During the surgical procedures, the light beam provided through lens holder 24 and lens 126 can be radiated into an eye being treated and provide an additional means for the physician to observe the point at which the surgical radiation is to impinge. Thus, the physician can not only see the A scan and B scan ultrasonic display of the eye tissue, but can also observe, from the side of transducer assembly 18, the point of orientation of the light beam provided through lens 126.

The arrangement for the transducer, which is shown in FIG. 2, facilitates surgical procedures including observation of surgical effects during the process of ultrasonic surgery. The effects of the therapeutic ultrasonic radiation from transducer 20 can be visually observed with the assistance of the light beam radiated through tube 24 and focused by lens 126. In addition to the visual observation, changes in tissue characteristics can be observed by observation of the displays of A scan and B scan ultrasonic echoes which are radiated and received through diagnostic transducer assembly 22. As an alternative to projection of light through optical channel 24, it is also possible to provide another separate light source and arrange for optical observation of tissue structure changes by modifying lens 126 to allow visual observation of tissue structure through optical channel 24.

An alternate surgical procedure using the transducer assembly 18 of FIG. 2 is to have the surgeon hold the transducer assembly 18 in his hand during examination and treatment. In this case, the physician can use the A scan display for purposes of tissue examination and for positioning and orienting transducer assembly 18.

Figure 5:
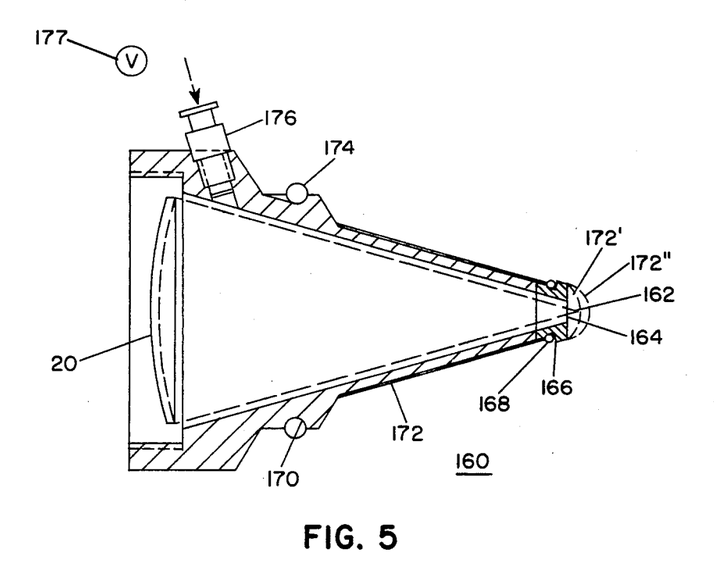
FIG. 5 is a cross sectional view of an alternate conical shell portion, useable with the transducer assembly of FIG. 2.

FIG. 5 is a cross sectional view of an alternate conical shell 160, which can be used instead of conical shell 128 on the transducer assembly 18 of FIG. 2. Conical shell 160 is adapted to thread onto housing member 76 in the same way as conical shell 128. Shell 160 is provided with a membrane 172 which is stretched across the conical surface and retained by O-rings 174 and 168 in circular grooves 170 and 166. The cavity within conical shell 160 is filled with fluid to surround transducer 20 and provide an efficient conductive medium for ultrasonic radiation. Shell 160 is provided with a fluid coupling 176 through which the cavity within the shell may be filled with fluid, for example, sterile distilled or saline water. In operation fluid under pressure may be supplied to shell 160 through a control valve or stopcock 177. The pressure of the fluid will cause the end of membrane 172 to bulge from the opening 164 at the apex of conical shell 160 as shown at 172' and 172". Stopcock 177 serves to stabilize the pressure and hold the bulge constant. This bulging of the membrane enables the direct application of conical shell 160 to the surface of an eye without the interposition of a fluid bath in a surgical fluid retaining drape surrounding the eye as described above. Accordingly, the draping process is unnecessary, and by direct application of a handheld transducer assembly with conical shell 160 to an eye the physician may perform both diagnostic and therapeutic ultrasonic radiation operations. As illustrated, the shell 160 has a relatively small aperture 164 which is located close to the focal point 162 of the radiation from transducer 20. This arrangement is particularly useful for treating areas close to the surface of the eye, for example, in the vicinity of the lens. It will be recognized, however, that by providing a larger aperture 164 which is further spaced from the focal point 162 of the transducer 20 it is possible to provide a greater spacing of the focal point of transducer operation from the end of shell 160 and therefore from the surface of the eye, for example, for surgery on the retina of the eye.

While there have been described what are believed to be the preferred embodiments of the present invention, those skilled in the art will recognize that other and further modifications may be made thereto without departing from the spirit of the invention and it is intended to claim all such changes and modifications as fall within the true scope of the invention.

We claim:

1. An ultrasonic transducer assembly, useful for non-invasive applications, comprising:
   a housing;
   a transducer means mounted within said housing for radiating a converging beam of acoustic energy in response to supplied electrical signals, said beam of acoustic energy converging to a focal point, said transducer having a central bore; and
   an alignment light source aligned with said transducer and mounted within said housing and through said transducer central bore for providing a spot of illumination at said focal point.

2. An ultrasonic therapeutic transducer assembly, useful for non-invasive treatment, comprising:
   a housing;
   a transducer mounted within said housing and comprising a spherical shell portion, said shell portion having an inner radius originating at a focal point, said transducer being responsive to electrical signals to emit a converging beam of acoustic energy toward said focal point, and said spherical shell portion having a central bore; and
   an alignment light source aligned with said transducer and located in said central bore for providing a light beam along a radius of said shell portion and a spot of illumination at said focal point.

3. A transducer assembly as specified in claim 1 or 2 wherein said housing includes means for maintaining fluid in contact with said transducer thereby to conduct said beam of acoustic energy.

4. An ultrasonic transducer assembly, useful for non-invasive diagnostics and therapy, comprising:
   a housing;
   a first transducer, mounted to said housing for radiating a first converging beam of acoustic energy in response to first supplied electrical signals, said first beam converging to a first focal point, and said first transducer having a first central bore;
   a second transducer, passing through said first central bore, for radiating and receiving a second converging beam of acoustic energy in response to second supplied electrical signals, said second beam converging to a second focal point, and said second transducer having a second central bore; and an alignment light source mounted in said second central bore and aligned with at least one of said transducers for providing a spot of illumination at the focal point of the transducer with which it is aligned.

5. An ultrasonic transducer assembly, useful for non-invasive diagnostics and therapy, comprising:
a first housing portion having a central bore;
a first transducer, mounted to said first housing portion and having a central bore aligned with said bore in said first housing, said first transducer for radiating a first converging beam of acoustic energy in response to supplied first electrical signals, said beam converging to a first focal point;
a second housing portion having a central bore and pivotably connected to said first housing portion adjacent said bore in said first housing portion at an end thereof opposite the direction of said first beam;
a second transducer, mounted to said second housing portion in said bore, and having a cylindrical transducer case extending through said bore in said first housing portion and said bore in said first transducer, said second transducer being responsive to second electrical signals for radiating and receiving a second beam of acoustic energy along an axis corresponding to the axis of said bore in said second housing portion; and
means for adjusting the pivotable connection between said first and second housing portions to cause said axis to be directed toward said focal point.

6. A transducer assembly as specified in claim 5 wherein said second beam converges to a second focal point, and wherein said second transducer is axially adjustable in said bore to cause said first and second focal points to have selected relative locations along said axis.

7. A transducer assembly as specified in claim 5 wherein said first housing portion further includes a cavity for retaining fluid adjacent the radiating surfaces of said first and second transducers.

8. A transducer assembly as specified in claim 7 wherein said bore of said first housing portion is provided with a moveable sealing member.

9. A transducer assembly as specified in claim 8 wherein said moveable sealing member comprises a toroidal undercut in said bore having a selected outer diameter, an O-ring in said undercut having an outer diameter smaller than said outer diameter of said undercut, an inner diameter corresponding to the diameter of said cylindrical transducer case and a thickness corresponding to the axial length of said toroidal undercut, and a viscous fluid in said undercut between said O-ring and said outer diameter of said undercut.

10. A transducer assembly as specified in claim 5 wherein said cavity includes a conical shell mounted to said first housing portion, said shell and said housing portion enclosing said first and second transducers.

11. A transducer assembly as specified in claim 5 wherein there is provided a central bore in said second transducer, and wherein there is provided an alignment light source in said central bore and aligned with at least one of said transducers for radiating light along said axis and for providing a spot of illumination at the focal point of the transducer with which it is aligned.

12. A transducer assembly as specified in claim 11 wherein said light source includes a lens and fiber optical means for providing light to said lens.

13. A transducer assembly useful for applying ultrasonic radiation to an eye, comprising:
a housing;
an ultrasonic transducer mounted to said housing and responsive to applied electrical signals for radiating a beam of acoustic energy along an axis toward a focal point;
a conical shell mounted to said housing and having a cone axis aligned with the beam axis and a geometrical cone apex and enclosing said transducer, said shell having an aperture at the apex end of said conical shell on said axis;
a flexible membrane over said aperture, said membrane maintaining fluid within said shell and having an outer contacting surface; and
means for increasing fluid pressure in said shell to cause said membrane to extend and protrude from said aperture and for adjusting the position of said contacting surface with respect to the focal point.

14. A transducer assembly, comprising:
a first hollow cylindrical housing member having first and second axial ends;
a transverse support member mounted within said cylindrical housing member and having a central bore extending in the axial direction of said cylinder;
a first piezoelectric transducer member comprising a circular spherical portion having inner and outer spherical surfaces with conductive films thereon, said transducer being sealingly mounted to said cylindrical housing at the outer periphery, and said transducer having a central bore aligned with said axial direction and being sealingly mounted to said support member at the periphery of said axial bore, said transducer being responsive to first electrical signals applied to said conductive films for radiating a converging first beam of acoustic energy to a focal point in said axial direction at the center of radius of said inner spherical surface;
a second housing member, pivotably mounted to said cylindrical housing member at an axial end thereof opposite said focal point, said second housing member having a central cylindrical bore axially adjacent said bore in said support member;
a second transducer, comprising a cylindrical transducer case mounted in said bore of said second housing member and extending through said bores in said support member and said first transducer, said second transducer having a central bore and having a radiating aperture at the axial end adjacent said focal point and being responsive to second electrical signals supplied thereto for radiating and receiving an acoustic beam of energy along the axis of said cylindrical case toward and from said focal point;
a moveable seal between said cylindrical transducer case and said transverse support member;
means for adjusting the pivot position of said second housing member with respect to said first housing member;
an alignment light source, mounted in said central bore in said second transducer and aligned with at least one of said transducers, for projecting a beam of light toward said focal point and for providing a spot of illumination at said focal point;

a shell forming a cavity enclosing said inner surface of said first transducer and said radiating aperture of said second transducer, said shell having an aperture at the end thereof adjacent said focal point and said shell being sealingly mounted to said cylindrical housing member; and a membrane covering said aperture for maintaining fluid in said cavity.

15. A transducer assembly as specified in claim 14 wherein there is further provided means for increasing fluid pressure in said cavity thereby to cause said membrane to form a bulbous protrusion from said aperture.

16. A transducer assembly as specified in claim 15 wherein the means for increasing fluid pressure comprises a stopcock to hold the fluid pressure relatively constant after the bulbous protrusion is formed.

17. An ultrasonic transducer assembly, useful for non-invasive applications, comprising:

a housing;

a transducer means mounted within said housing for radiating a beam of acoustic energy toward a focal point in response to supplied electrical signals; and an alignment light source for emitting a light beam, said source being mounted within said housing and aligned with said transducer for providing a spot of illumination at said focal point to provide a visual indication of the acoustic energy beam.

18. A system for performing ultrasonic therapeutic surgery, comprising:

a transducer assembly, moveable by a surgeon for radiating a therapeutic ultrasonic beam and a diagnostic ultrasonic beam into a patient;

optical means coupled to said transducer assembly, for providing an optical channel in the direction of said ultrasonic beams;

an alignment light source aligned with at least one of said ultrasonic beams for providing a visual indication specifying the path of said one beam;

means coupled to said transducer assembly for transmitting and receiving diagnostic ultrasonic signals and for displaying said received signals on a visual display;

and means coupled to said transducer for providing a timed burst of relatively high energy therapeutic ultrasonic signals to said transducer assembly;

whereby tissue characteristics can be observed on said display and by use of said optical channel, while said therapeutic ultrasonic beam performs tissue modification.

19. A method for performing ultrasonic surgery comprising the steps of:

transmitting and receiving ultrasonic signals from tissue upon which surgery is to be performed along a beam axis with at least one transducer;

processing said received ultrasonic signals to generate a visual display representation of tissue characteristics;

illuminating said tissue with an alignment light source aligned with said transducer and positioned to project light along the beam axis for providing a visual indication of the acoustic beam axis;

modifying the tissue by irradiating said tissue with relatively high energy ultrasonic radiation;

and visually observing said illuminated tissue, during said irradiation.

20. An ultrasonic transducer assembly, useful for non-invasive applications, comprising:

a housing;

a transducer mounted within said housing for radiating a beam of acoustic energy in response to supplied electrical signals; and an alignment light source for emitting a light beam, said source being mounted within said housing and aligned with said transducer for providing a visual indication of the acoustic energy beam.

* * * * *

UNITED STATES PATENT AND TRADEMARK OFFICE
CERTIFICATE OF CORRECTION

PATENT NO. : 4,484,569

DATED : November 27, 1984

INVENTOR(S) : Driller et al.

It is certified that error appears in the above-identified patent and that said Letters Patent is hereby corrected as shown below:

First page, delete Item [30], since no priority has been claimed;
Column 5, line 49, "forwrd" should read --forward--;
Column 8, line 36, after "point" insert --to provide a visual indication of the acoustic energy beam--;
Column 8, line 50, after "point" insert --to provide a visual indication of the acoustic energy beam--;
Column 12, lines 34 and 35, after "light source" delete "for emitting a light beam, said sourve being" and insert a comma;
Column 12, line 36, after "transducer" insert --, for projecting a beam of light along said acoustic energy beam axis and forming a spot of illumination corresponding to the location of said beam axis on a surface intersecting said axis,--.

Signed and Sealed this

Twenty-ninth Day of October 1985

[SEAL]

Attest:

DONALD J. QUIGG

Attesting Officer

Commissioner of Patents and
Trademarks—Designate